(12) United States Patent
Schneider et al.

(10) Patent No.: US 12,030,899 B2
(45) Date of Patent: Jul. 9, 2024

(54) Pt-BIPHENYL-IODINE COMPLEX AND Pt-BIPHENYL-BROMINE COMPLEX

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OXENO GMBH & CO. KG, Marl (DE)

(*) Notice: Subject to any disclaimer, the term of this patent is extended or adjusted under 35 U.S.C. 154(b) by 0 days.

(21) Appl. No.: 18/064,953

(22) Filed: Dec. 13, 2022

(65) Prior Publication Data

US 2023/0192743 A1    Jun. 22, 2023

(30) Foreign Application Priority Data

Dec. 17, 2021    (EP) .................... 21215366

(51) Int. Cl.
  *C07F 15/00* (2006.01)
  *B01J 31/22* (2006.01)
  *C07C 45/50* (2006.01)

(52) U.S. Cl.
  CPC ....... *C07F 15/0093* (2013.01); *B01J 31/2208* (2013.01); *C07C 45/505* (2013.01)

(58) Field of Classification Search
  CPC .............. C07F 15/0093; C07F 15/0086; B01J 31/2208; B01J 23/42; C07C 45/505
  See application file for complete search history.

(56) References Cited

U.S. PATENT DOCUMENTS

| | | | | |
|---|---|---|---|---|
| 4,668,651 A | * | 5/1987 | Billig | B01J 31/185 502/166 |
| 5,264,616 A | * | 11/1993 | Roeper | C07C 67/347 560/177 |
| 5,962,744 A | | 10/1999 | Ojima et al. | |
| 6,172,267 B1 | * | 1/2001 | Urata | C07C 45/50 568/454 |
| 6,300,515 B1 | * | 10/2001 | Retboll | C07C 67/293 560/244 |
| 2013/0324756 A1 | | 12/2013 | Kreidler et al. | |
| 2023/0191384 A1 | | 6/2023 | Schneider et al. | |
| 2023/0191385 A1 | | 6/2023 | Schneider et al. | |
| 2023/0192581 A1 | | 6/2023 | Schneider et al. | |
| 2023/0192582 A1 | | 6/2023 | Schneider et al. | |
| 2023/0192583 A1 | | 6/2023 | Schneider et al. | |
| 2023/0192584 A1 | | 6/2023 | Schneider et al. | |
| 2023/0192740 A1 | | 6/2023 | Schneider et al. | |
| 2023/0192741 A1 | | 6/2023 | Schneider et al. | |
| 2023/0192742 A1 | | 6/2023 | Schneider et al. | |

FOREIGN PATENT DOCUMENTS

| | | |
|---|---|---|
| EP | 2663573 B1 | 6/2016 |
| GB | 1 368 434 | 9/1974 |
| WO | 99/50214 A1 | 10/1999 |

OTHER PUBLICATIONS

M. Muelhofer, et.al. 660, Journal of Organometallic Chemistry, 121-126 (2002) (Year: 2002).*
M. Hariharasarma, et.al. 18, Organometallics 2593-2600 (1999) (Year: 1999).*
European Search Report mailed May 30, 2022 for European Patent Application No. 21215366.2 (8 pages in German with English Translation).
Hariharasarma, M., et al. X-ray crystal structure of cis={(±)-6,6'-[[1,1'-biphenyl]-2,2'-diylbis(oxy)]bisdibenzo[d,f][1,3,2]dioxaphosphepin}diiodoplatinum(II) dichloromethane. Journal of Chemical Crystallography.1999. pp. 87-91.
U.S. Appl. No. 18/064,945, Schneider et al., filed Dec. 13, 2022.
U.S. Appl. No. 18/064,946, Schneider et al., filed Dec. 13, 2022.
U.S. Appl. No. 18/064,947, Schneider et al., filed Dec. 13, 2022.
U.S. Appl. No. 18/064,948, Schneider et al., filed Dec. 13, 2022.
U.S. Appl. No. 18/064,949, Schneider et al., filed Dec. 13, 2022.
U.S. Appl. No. 18/064,950, Schneider et al., filed Dec. 13, 2022.
U.S. Appl. No. 18/064,952, Schneider et al., filed Dec. 13, 2022.
U.S. Appl. No. 18/064,955, Schneider et al., filed Dec. 13, 2022.
U.S. Appl. No. 18/064,958, Schneider et al., filed Dec. 13, 2022.
Communication from the Examination division mailed Aug. 21, 2023 for European Patent Application No. 21 215 366.2 (4 pages in German with English translation).
Zhang, Y., et al. Binuclear Pd(I)-Pd(I) Catalysis Assisted by Iodide Ligands for Selective Hydroformylation of Alkenes and Alkynes. Journal of American Chemical Society. 2020, vol. 142, pp. 18251-18265.

* cited by examiner

*Primary Examiner* — Alexander R Pagano
(74) *Attorney, Agent, or Firm* — Smith, Gambrell & Russell, LLP

(57) ABSTRACT

Pt-biphenyl-iodine complex and Pt-biphenyl-bromine complex, and the use thereof for catalysis of a hydroformylation reaction.

11 Claims, No Drawings

Pt-BIPHENYL-IODINE COMPLEX AND Pt-BIPHENYL-BROMINE COMPLEX

The present invention relates to a Pt-biphenyl-iodine complex and Pt-biphenyl-bromine complex, and the use thereof for catalysis of a hydroformylation reaction.

EP 2663573 B1 describes a process for the preparation of (1).

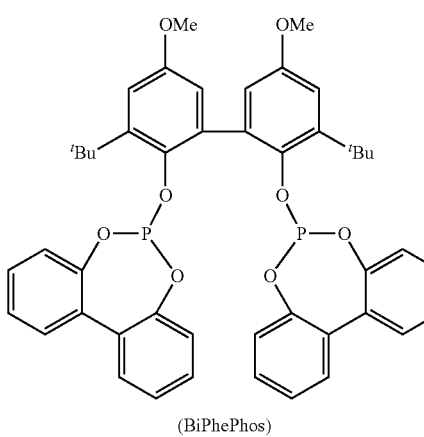

(BiPhePhos)

It was an object of the present invention to provide a novel complex. In the case of catalysis of hydroformylation reactions, the complex should afford an increased yield.

This object is achieved by a complex according to claim 1.

Complex comprising:
a) Pt;
b) a ligand corresponding to formula (I):

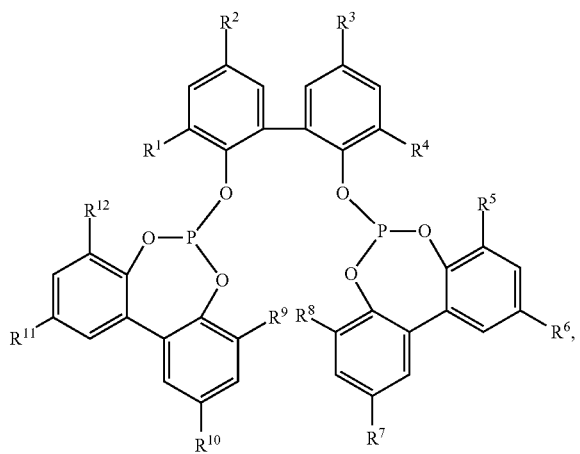

where $R^1, R^2, R^3, R^4, R^5, R^6, R^7, R^8, R^9, R^{10}, R^{11}, R^{12}$ are selected from: —H, —($C_1$-$C_{12}$)-alkyl, —O—($C_1$-$C_{12}$)-alkyl, —($C_6$-$C_{20}$)-aryl;

c) an iodine ligand or a bromine ligand.

The expression ($C_1$-$C_{12}$)-alkyl encompasses straight-chain and branched alkyl groups having 1 to 12 carbon atoms. These are preferably ($C_1$-$C_8$-alkyl groups, more preferably ($C_1$-$C_6$)-alkyl, most preferably ($C_1$-$C_4$)-alkyl.

Suitable ($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The definition of ($C_1$-$C_{12}$)-alkyl also applies analogously to the ($C_1$-$C_{12}$)-alkyl in —O—($C_1$-$C_{12}$)-alkyl.

The expression ($C_6$-$C_{20}$)-aryl encompasses mono- or polycyclic aromatic hydrocarbon radicals having 6 to 20 carbon atoms. These are preferably ($C_6$-$C_{14}$)-aryl, more preferably ($C_6$-$C_{10}$)-aryl.

Suitable ($C_6$-$C_{20}$)-aryl groups are especially phenyl, naphthyl, indenyl, fluorenyl, anthracenyl, phenanthrenyl, naphthacenyl, chrysenyl, pyrenyl, coronenyl. Preferred ($C_6$-$C_{20}$)-aryl groups are phenyl, naphthyl and anthracenyl.

In one embodiment, $R^1, R^2, R^3, R^4$ are selected from: —($C_1$-$C_{12}$)-alkyl, —O—($C_1$-$C_{12}$)-alkyl.

In one embodiment, $R^1$ and $R^4$ are —($C_1$-$C_{12}$)-alkyl.

In one embodiment, $R^1$ and $R^4$ are —$^t$Bu.

In one embodiment, $R^2$ and $R^3$ are —O—($C_1$-$C_{12}$)-alkyl.

In one embodiment, $R^2$ and $R^3$ are —OMe.

In one embodiment, $R^5, R^6, R^7, R^8, R^9, R^{10}, R^{11}, R^{12}$ are —H.

In one embodiment, the compound of formula (I) has the structure (1):

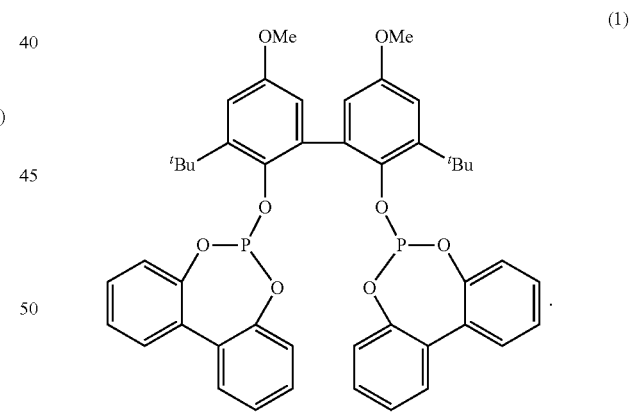

In one embodiment, the complex has exactly one ligand corresponding to formula (I).

In one embodiment, the complex has at least two iodine ligands.

In one embodiment, the complex has exactly two iodine ligands.

In one embodiment, the complex has at least two bromine ligands.

In one embodiment, the complex has exactly two bromine ligands.

As well as the complex per se, the use thereof for catalysis of a hydroformylation reaction is also claimed.

Use of a complex as described above for catalysis of a hydroformylation reaction.

The invention shall be elucidated in more detail hereinbelow with reference to working examples.

EXPERIMENTAL DESCRIPTION

A vial was charged with $PtX_2$ (X=halogen), ligand, and an oven-dried stirrer bar. The vial is then sealed with a septum (PTFE-coated styrene-butadiene rubber) and phenolic resin cap. The vial is evacuated and refilled with argon three times. Toluene and 1-octene were added to the vial using a syringe. The vial was placed in an alloy plate, which was transferred to an autoclave of the 4560 series from Parr Instruments under an argon atmosphere. After purging the autoclave three times with $CO/H_2$, the synthesis gas pressure was increased to 40 bar at room temperature. The reaction was conducted at 120° C. for 20 h. On termination of the reaction, the autoclave was cooled to room temperature and cautiously decompressed. Yield and selectivity were determined by GC analysis.

Variation of the Halogen

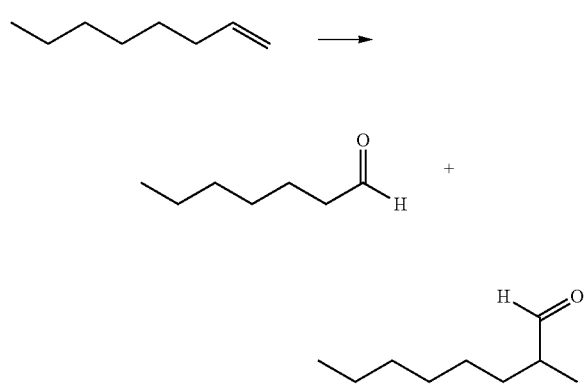

Reaction Conditions:

1.0 mmol of 1-octene, 1.0 mol % $PtX_2$, 2.2 equivalents of ligand (1), solvent: toluene, $p(CO/H_2)$: 40 bar, T: 120° C., t: 20 h.

Yields:

| Ligand | Halogen | Yield [%] |
|---|---|---|
| 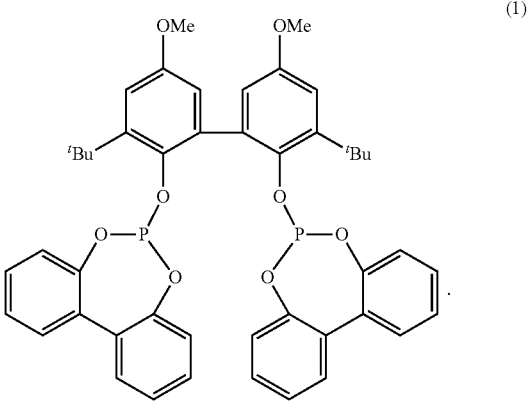 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1] (1) | I/Br | 69/27 |

As the experimental results show, the object is achieved by the complex according to the invention.

The invention claimed is:

1. A complex comprising:
   a) Pt;
   b) a ligand corresponding to formula (I):

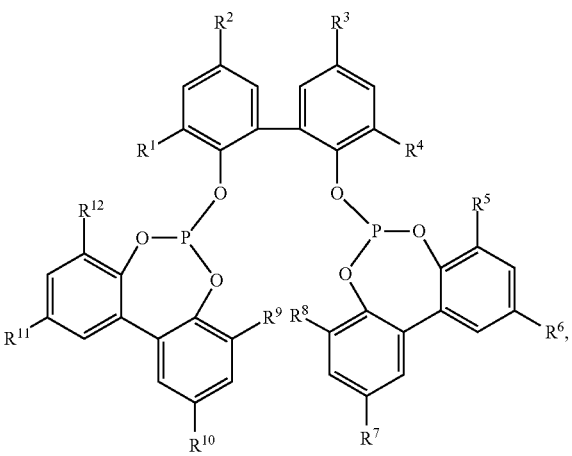

where $R^1$, $R^2$, $R^3$ and $R^4$ are selected from: —$(C_1$-$C_{12})$-alkyl or —O—$(C_1$-$C_{12})$-alkyl, and $R^5$, $R^6$, $R^7$, $R^8$, $R^9$, $R^{10}$, $R^{11}$ and $R^{12}$ are selected from: —H, —$(C_1$-$C_{12})$-alkyl, —O—$(C_1$-$C_{12})$-alkyl or —$(C_6$-$C_{20})$-aryl;
   c) an iodine ligand or a bromine ligand.

2. The complex according to claim 1, where $R^1$ and $R^4$ are —$(C_1$-$C_{12})$-alkyl.

3. The complex according to claim 1, where $R^2$ and $R^3$ are —O—$(C_1$-$C_{12})$-alkyl.

4. The complex according to claim 1, where $R^5$, $R^6$, $R^7$, $R^8$, $R^9$, $R^{10}$, $R^{11}$ and $R^{12}$ are —H.

5. The complex according to claim 1, wherein the compound of formula (I) has the structure (1):

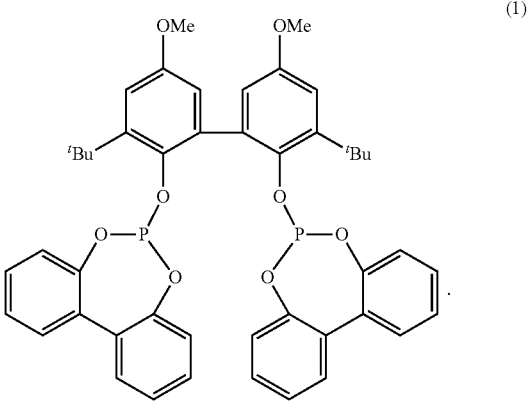 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

6. The complex according to claim 1, wherein the complex has exactly one ligand corresponding to formula (I).

7. The complex according to claim 1, wherein the complex has two iodine ligands.

8. The complex according to claim 7, wherein the complex has exactly two iodine ligands.

9. The complex according to claim 1, wherein the complex has at least two bromine ligands.

10. The complex according to claim 9, wherein the complex has exactly two bromine ligands.

11. In a hydroformylation process comprising contacting a hydroformylation substrate with a catalyst, wherein the improvement comprises contacting the hydroformylation substrate with a complex according to claim 1.

\* \* \* \* \*